(12) United States Patent
Berg Van Den et al.

(10) Patent No.: US 6,989,461 B2
(45) Date of Patent: Jan. 24, 2006

(54) CATALYST FOR ASYMMETRIC (TRANSFER) HYDROGENATION

(75) Inventors: Michel Berg Van Den, Groningen (NL); Ben Feringa, Paterswolde (NL); Adriaan Jacobus Minnaard, Zuidhorn (NL); Johannes Gerardus Vries De, Maastricht (NL)

(73) Assignee: DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 10/332,403

(22) PCT Filed: Jul. 6, 2001

(86) PCT No.: PCT/NL01/00517

§ 371 (c)(1),
(2), (4) Date: Jan. 7, 2003

(87) PCT Pub. No.: WO02/04466

PCT Pub. Date: Jan. 17, 2002

(65) Prior Publication Data

US 2003/0199713 A1 Oct. 23, 2003

(30) Foreign Application Priority Data

Jul. 7, 2000 (NL) .............................. 1015655

(51) Int. Cl.
C07C 229/00 (2006.01)
C07C 67/00 (2006.01)
B01J 31/00 (2006.01)

(52) U.S. Cl. ............................. 560/40; 560/41; 560/99; 502/162

(58) Field of Classification Search ................. 502/162; 560/40, 41, 99

See application file for complete search history.

(56) References Cited

U.S. PATENT DOCUMENTS 4,414,345 A * 11/1983 Rasberger ................... 524/108

FOREIGN PATENT DOCUMENTS

WO   WO 01/00581        1/2001
WO   WO 01/00581 A1 *   1/2001
WO   WO 01/09147        2/2001

OTHER PUBLICATIONS

Van den Berg et al, Journal of the American Chemical Society, 2000, 122(46), pp. 11539–11540.*
Francio et al, Angewandte Chemie International Edition, 2000, 39(8), pp. 1428–1430.*
Alexakis, A. et al., "Asymmetric Conjugate Addition of Diethyl Zinc to Enones with Chiral Phosphorus Ligands Derived from TADDOL" Tetrahedron Letters 39(43):7869–7872 (1998).

Arnold, L. A., et al., "Enantioselective Catalytic Conjugate Addition of Dialkylzinc Reagents Using Copper–Phosphoramidite Complexes; Ligand Variation and Non–Linear Effects" Tetrahedron 56(18):2865–2878 (2000).
Bartels, B., "Ir–Catalysed Allylic Substitution: Mechanistic Aspects and Asymmetric Synthesis with Phosphorus Amidites as Ligands" Journal of the Chemical Society 8:741–742 (1999).
Bertozzi, F. et al., "A New Diastereo– and Enantioselective Copper–Catalyzed Conversion of Alkynyl Epoxides into Alpha–Allenic Alcohols" Tetrahedron Letters 40(26):4893–4896 (1999).
Brown, J.M., Comprehensive Asymmetric Catalysis E.N. Jacobsen, A. Pfaltz and H. Yamamoto (Eds.) Springer, Berlin 1999 vol. 1, pp. 121–182.
De Vries, A.H.M., "Enantioselective Conjugate Addition of Dialkylzinc Reagents to Cyclic and Acyclic Enones Catalyzed by Chiral Copper Complexes of New Phosphorus Amidites" Angewandte Chemi. 35(20):2374–2376 (1996).
Francio, et al., "Asymmetric Catalysis with Chiral Phosphane/Phosphoramidite Ligands Derived from Quinoline (QUINAPHOS)" Angewandte Chemie 39(8):1428–1430 (2000).
International Search Report for PCT/NL01/00517, mailed on Jan. 3, 2002, 5 pages.
Keller, E. et al., "Unexpected Enhancement of Enantioselectivity in Copper (II) Catalyzed Conjugate Addition of Diethylzinc to Cyclic Enones with Novel TADDOL Phosphorus Amidite Ligands" Tetrahedron 9(14):2409–2413 (1998).

(Continued)

Primary Examiner—Paul A. Zucker
(74) Attorney, Agent, or Firm—Morrison & Foerster LLP

(57) ABSTRACT

Catalyst for the asymmetric (transfer) hydrogenation represented by the formula $ML_aX_bS_c$, where M is a transition metal, to be chosen from rhodium and ruthenium, and X is a counter ion and S is a ligand, a ranges from 0.5 to 3 and b and c, each independently, range from 0 to 2, and L is a chiral ligand having the formula (1), where $C_n$ together with the two 2 O-atoms and the P-atom forms a substituted or non-substituted ring with 2–4 C-atoms, $R^1$ and $R^2$ each independently represent H, an optionally substituted alkyl, aryl, alkaryl or aralkyl group or may form a (heterocyclic) ring together with the N-atom to which they are bound. And a process for the asymmetric (transfer) hydrogenation of an olefinically unsaturated compound, ketone, imine or oxime derivate in the presence of a hydrogen donor and of a catalyst, use being made of a catalyst represented by formula $ML_aX_bS_c$, where M is a transition metal, to be chosen from rhodium, iridium and ruthenium, X is a counter ion, S is a ligand, a ranges from 0.5 to 3 and b and c range from 0 to 2, and L is a chiral ligand having the formula (1), where $C_n$ together with the two 2 O-atoms and the P-atom forms a substituted or non-substituted ring with 2–4 C-atoms; and $R^1$ and $R^2$ are as defined above.

18 Claims, No Drawings

OTHER PUBLICATIONS

Nifantyev, E.E., "Pentose Amidophosphites, Synthesis, Palladium Complexes" Phosphorus Sulfur and the Related Elements 12(1):27–36 (1981).

Sewald, N. et al., "Enantioselective Copper (I) Catalyzed 1,4–Addition of Diethylzinc to Nitroolefins" Tetrahedron 9(8):1341–1344 (1998).

Van Den Berg, M., "Highly Enantioselective Rhodium–Catalyzed Hydrogenation with Monodentate Ligands" Journal of the American Chemical Society 122(46):11539–11540 (2000).

Welton, T., Chem. Rev. 99:2071–2083 (1999).

* cited by examiner

CATALYST FOR ASYMMETRIC (TRANSFER) HYDROGENATION

This application is a 35 U.S.C. § 371 national stage application of PCT International Application No. PCT/NL01/00517, filed on Jul. 6, 2001, which claims foreign priority benefits under 35 U.S.C. § 119(a) and/or § 365(b) of Netherlands Patent Application No. 1015655, filed Jul. 7, 2000.

The invention relates to a catalyst for the asymmetric (transfer) hydrogenation that contains a transition metal compound and a chiral ligand.

Such catalysts are known from G. Franciò, F. Faraone and W. Leitner, *Angewandte Chemie. Int. Ed.* 2000, 39, 1428–1430. This publication describes the use of bidentate phosphine phosphorus amidite ligands for the asymmetric hydrogenation of substituted olefins with enantioselectivities of up to 98.8%.

A drawback of the known catalysts is that the ligands used are generally prepared via many reaction steps, a number of which often proceed with a low yield. This makes these ligands extremely expensive. Another drawback of these phosphine containing ligands is that they are relatively sensitive to oxygen, which causes problems in handling them in practice.

The invention now provides a catalyst consisting of a transition metal catalyst and a chiral ligand in which the ligand can simply be prepared in one or two steps from commercially available starting materials.

According to the invention this is achieved with a catalyst represented by the formula $ML_aX_bS_c$, where M is a transition metal, to be chosen from rhodium and ruthenium, L is an enantiomerically enriched chiral monodentate ligand having the formula (I),

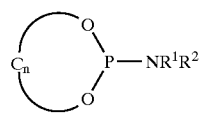
(I)

where $C_n$ together with the two O-atoms and the P-atom forms a substituted or non-substituted ring with 2–4 C-atoms, $R^1$ and $R^2$ each independently stand for H, an optionally substituted alkyl, aryl, aralkyl or alkaryl group, or may form a (heterocyclic) ring together with the N-atom to which they are bound, X is a counter ion and S is a ligand, a ranges from 0.5 to 3, b and c each independently range from 0 to 2. Preferably $R^1$ and $R^2$ each independently represent an alkyl group, for instance an alkyl group with 1–6 C-atoms, in particular 1–3 C-atoms, most preferably $C_1$ and $C_2$ represent a methyl group. The alkyl, aryl, aralkyl and alkaryl groups preferably have 1–20 C-atoms and can optionally be substituted with for instance one or more hydroxy, alkoxy, nitrile or carboxylic ester groups, or halogens. $R^1$ and/or $R^2$ may be part of a polymeric backbone.

It has, surprisingly, been found that a high enantioselectivity can be achieved in the asymmetric hydrogenation or asymmetric transfer hydrogenation of olefins, ketones and imines when using the monodentate ligands of formula (I), which can be prepared in a simple manner. This is all the more surprising since it is generally assumed that bidentate ligands are needed to achieve a high enantioselectivity. Another advantage of the catalysts according to the invention is that the reaction rate increases with increasing pressure, without the enantioselectivity decreasing. As a result, a lower amount of catalyst will suffice or a faster reaction can be obtained. Yet another advantage is that the ligands according to the invention are virtually not sensitive to oxygen. Using a catalyst according to the invention in the asymmetric (transfer) hydrogenation of a prochiral compound, enantiomerically enriched compounds can be obtained with an ee of >90%, in particular >95%, more in particular >98%.

The catalyst according to the invention represented by the formula $ML_aX_bS_c$ may be neutral, anionic or cationic. The catalyst according to the invention may consist of a preformed complex having the formula $ML_aX_bS_c$. These complexes can be prepared by reacting the chiral ligand with a catalyst precursor. Preferably, however, the catalyst is formed in situ by adding the chiral ligand to a solution of a catalyst precursor which may contain a ligand that is easily removed by hydrogenation. The amount of optically active ligand to be added for example may range from 0.5 to 5, preferably from 1 to 3.5, equivalents relative to the metal. Preferably a small excess of optically active ligand is applied relative to the desired amount of optically active ligand in the catalyst. The optimum ratio of optically active ligand to metal in the catalyst may differ per optically active ligand and per metal and can readily be determined by means of experiments.

The catalyst can be activated by means of hydrogenation (prehydrogenation) prior to the addition of the substrate. It has been found that without this pretreatment of the catalysts according to the invention the same or an even higher enantioselectivity is achieved.

Examples of suitable catalyst precursors are (COD=1,5 cyclooctadiene; nbd=norbornadiene; L=ligand I; S=a ligand as defined below): $[Rh(COD)_2Cl]_2$, $[Rh(COD)_2)]BF_4$, $[Rh(nbd)_2]BF_4$, $[Rh(nbd)_2]ClO_4$, $[Ru(COD)Cl_2]_n$, $RhCl_3 \cdot nH_2O$, $Ru(OAc)_3$, $RuCl_3 \cdot nH_2O$. Examples of preformed complexes are $RhL_2(CH_3OH)_2BF_4$, $Rh(COD)L_2BF_4$, $RuL_2(OAc)_2$, $RuL_2Br_2$, $Ru(methylallyl)_2L_2$, $Ru(eta-6-benzene)L_2Br_2$, $Ru(eta-5-cyclopentadienyl)L_2Cl$, $RuL_2Cl_2$, $RuLSCl_2$, $Ru(1,2-diphenyl-1,2-diaminoethane)LCl_2$.

In the chiral ligand L of formula (I) $C_n$ and/or $R^1$ and/or $R^2$ are chiral or are part of a chiral entity. $C_n$ preferably represents a chiral substituted $C_4$ chain (chain with 4 optionally substituted C-atoms), of predominantly one configuration, for example with an enantiomeric excess larger than 95%, in particular larger than 99%, more in particular larger than 99.5%. Preferably $C_n$ together with the two O-atoms and the P-atom forms a 7-membered ring with 4 C-atoms which 2 by 2 form part of an aryl group or a naphthyl group. Examples of suitable chiral ligands according to the invention are

1

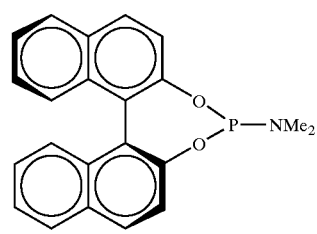

-continued
2
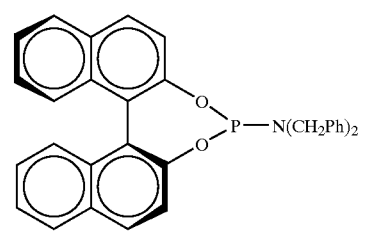
3
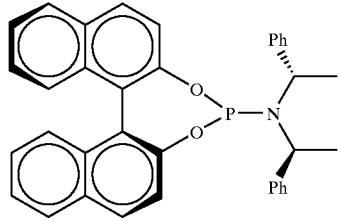
4
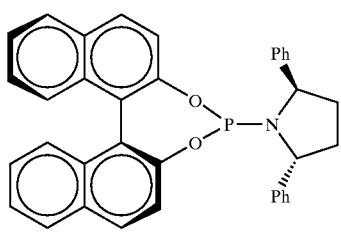
5
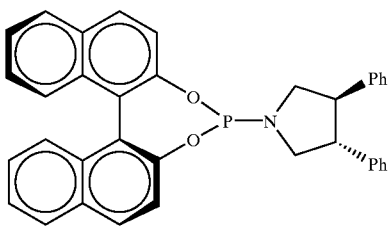
6
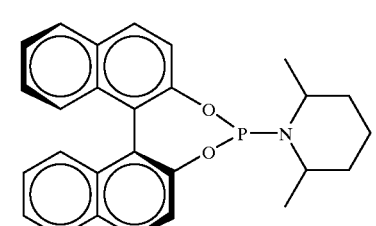
2a
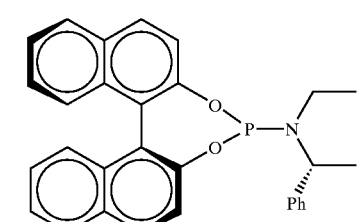
7
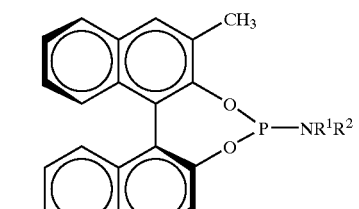
($R^1$ and $R^2$ see text above)
-continued
8
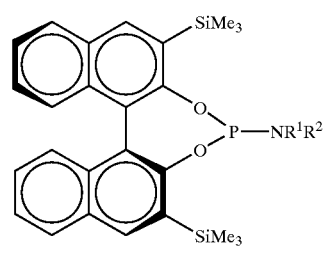
($R^1$ and $R^2$ see text above)
9
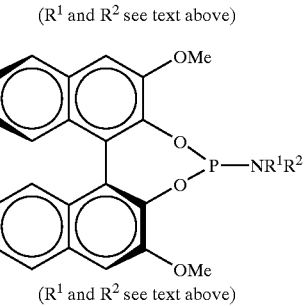
($R^1$ and $R^2$ see text above)
10
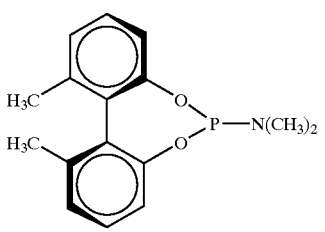
11
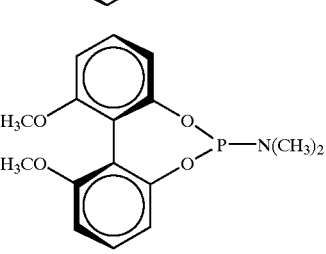
12
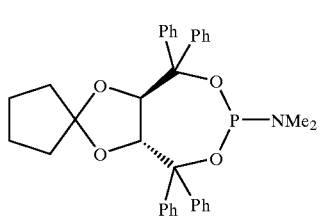
13
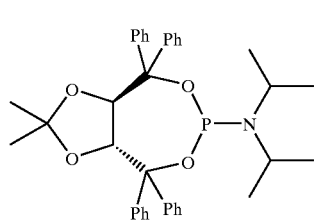
14
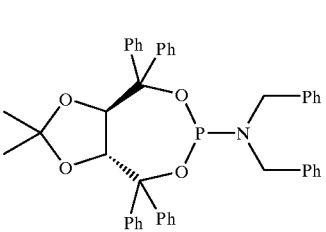

15
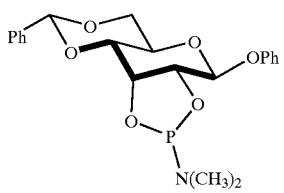
16
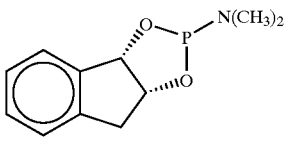
17
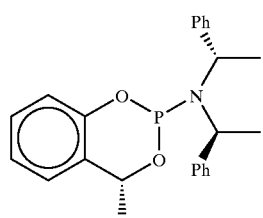
18
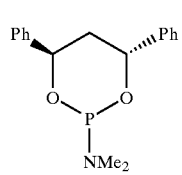
19
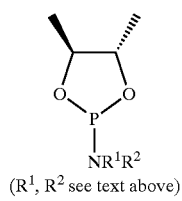
(R¹, R² see text above)
20
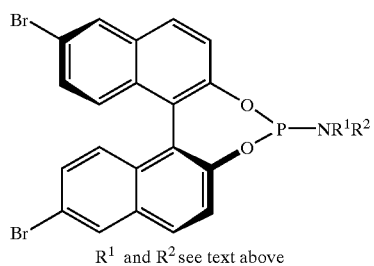
R¹ and R² see text above
21
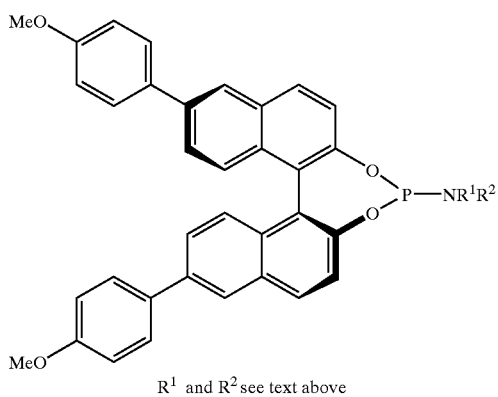
R¹ and R² see text above
22
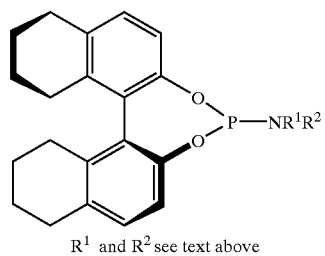
R¹ and R² see text above
23
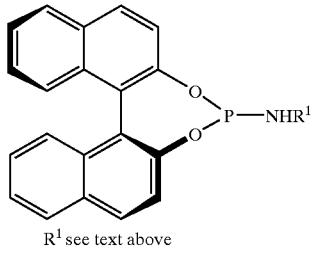
R¹ see text above
24
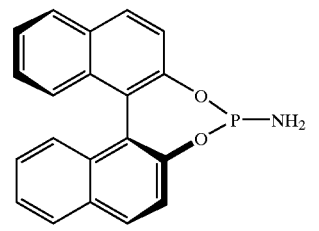
25
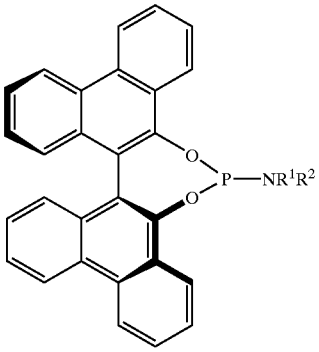
R¹ and R² see text above
26
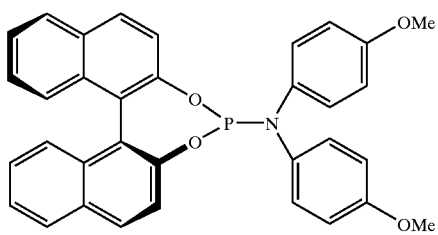
27
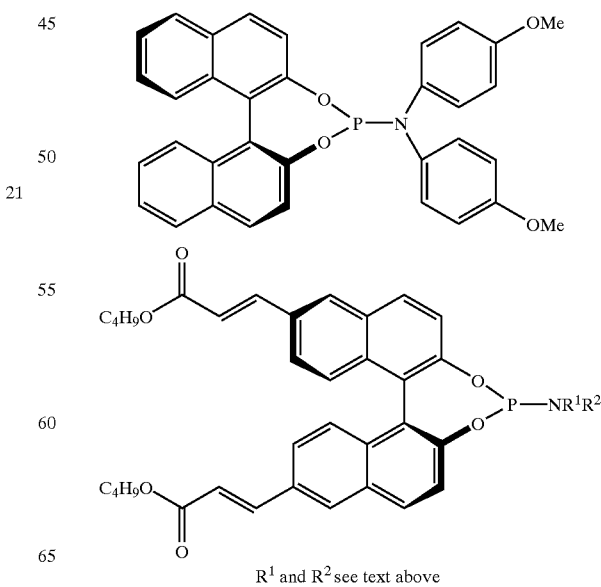
R¹ and R² see text above It will be understood that where one enantiomer is represented, the other enantiomer is similarly applicable.

Such ligands with formula (I) can simply be prepared as described for example in *Houben-Weyl Methoden der Organischen Chemie Band*XII/2. *Organische phosphorverbindungen*. G. Thieme Verlag, Stuttgart, 1964, Teil 2 (4th ed.), pp. 99–105. A preferred preparation method is based on the reaction of an HO—$C_n$—OH compound with P(NMe$_2$)$_3$ or P(NEt$_2$)$_3$ (Me=methyl, Et=ethyl), with subsequent reaction with R$^1$R$^2$NH, preferably in a solvent having a boiling point >80° C., for example toluene. Examples of suitable catalysts for the latter reaction are ammonium chloride, tetrazole or benzimidazoliumtriflate. Examples of HO—$C_n$—OH are chiral bisnaphtols for example (R)- or (S)-1,1'-bi-(2-naphthol), chiral bisphenols for example (R)- or (S)-6,6'-dimethoxy-2,2'-bisphenol, diols, for example (R,R)- or (S,S)-2,2-dimethyl-1,3-dioxolane-4,5-bis-(1,1-diphenyl) methanol (TADDOL), or (S,R) or (R,S)-indane-1,2-diol; 1,2-diols and 1,3-diols based on sugars, for example diols having the formula:

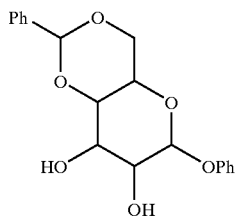

Examples of R$^1$R$^2$NH are benzyl amine, dibenzyl amine, diisopropyl amine, (R)- or (S)-1-methyl-benzyl amine, piperidine, morpholine, (R,R)- or (S,S)-bis-(1-methylbenzyl)amine.

A second preferred preparation is based on the reaction of an HO—$C_n$—OH compound with PCl$_3$, with subsequent reaction with R$^1$R$^2$NH, preferably in the presence of a base, for example Et$_3$N, and in the presence of a solvent, for example toluene. Examples of HO—$C_n$—OH are in principle the same as mentioned above in relation to the first preferred preparation. Examples of R$^1$R$^2$NH are ammonia, benzyl amine, dibenzyl amine, diisopropyl amine, (R)- or (S)-1-methyl-benzyl amine, piperidine, morpholine, (R,R)- or (S,S)-bis-(1-methylbenzyl)amine.

If the catalyst of the invention with the formula ML$_a$X$_b$S$_c$ is cationic, then the counter ion X is an anion. Examples of suitable anions are Cl, Br, I, OAc, BF$_4$, PF$_6$, ClO$_4$, p-toluene sulphonate, benzene phosphonate, tetrapentafluorophenylborate. Non-coordinating anions are preferred. If the catalyst is anionic, X is a cation. Examples of suitable cations are alkaline metals, for example Li, Na or K, alkaline earth metals such as Mg or Ca, or ammonium, or alkyl-substituted ammonium.

Ligand S may be chiral or non chiral. Suitable ligands S are olefins, for example maleic anhydride or ethylene; dienes, for example 1,5-cyclooctadiene, 1,3-butadiene and 2,5-norbornadiene; aromatics, for example benzene, hexamethyl benzene, cymene and cumene, eta-5 coordinated cyclopentadienyl ligands, for example cyclopentadienyl and pentamethyl-cyclopentadienyl, diamines such as 1,2-diaminoethane. Examples of chiral ligands S are (R,R)-1,2-cyclohexanediamine, (S,S)-1,2-diphenyl-1,2-diaminoethane, (S,S)-1,2-dicyclohexyl-1,2-diaminoethane or (S)-1,1'-bis(p-methoxyphenyl)-1,2-propanediamine.

The invention also relates to the preparation of the chiral ligands of formula I. In addition, the invention relates to the use of a catalyst represented by the formula ML$_a$X$_b$S$_c$, where M is a transition metal, to be chosen from rhodium, iridium and ruthenium, and X is a counter ion and S is a ligand, a ranges from 0.5 to 3 and b and c, each independently, range from 0 to 2, wherein L is a chiral ligand of formula (I)

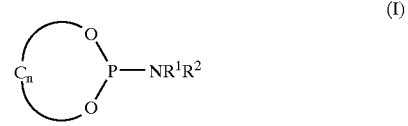

(I)

where $C_n$ together with the two O-atoms and the P-atom forms a substituted or non-substituted ring with 2–4 C-atoms; and R$^1$ and R$^2$ are as defined above, in the asymmetric hydrogenation or in the asymmetric transfer hydrogenation of for example olefins, ketones, imines and oxime derivates. $C_n$ and/or R$^1$ and/or R$^2$ are chiral or are part of a chiral entity. Examples of suitable catalyst precursors, which together with the chiral ligand form the catalyst, are (COD=1,5 cyclooctadiene; nbd=norbornadiene L=ligand I of the invention, S=a ligand as defined above): [Rh (COD) Cl]$_2$, [Rh(COD)$_2$]BF$_4$, [Rh(nbd)$_2$]BF$_4$, [Rh(nbd)$_2$]ClO$_4$, [Ir (COD)Cl]$_2$, [Ir(COD)$_2$]X (X=BF$_4$, PF$_6$, ClO$_4$, SbF$_6$, CF$_3$SO$_3$, B(C$_6$F$_5$)$_4$), [Ru(COD)Cl$_2$]$_n$. Examples of preformed complexes are RhL$_2$(CH$_3$OH)$_2$BF$_4$, Rh(COD)L$_2$BF$_4$, RuL$_2$(OAc)$_2$, RuL$_2$Br$_2$, Ru(methylallyl)$_2$L$_2$, Ru(eta-6-benzene)L$_2$Br$_2$, Ru(eta-5-cyclopentadienyl)L$_2$Cl, RuLSCl$_2$, Ru(1,2-diphenyl-1,2-diaminoethane)LCl$_2$, IrL$_2$(CH$_3$OH)$_2$PF$_6$, Ir(COD)L$_2$BF$_4$.

In the preparation of the catalyst preferably a molar ratio of metal to the optically active ligand of between 2:1 and 1:10, preferably between 1:1 and 1:6, is chosen. Preferably the catalyst is prepared in situ, which means in the same pot as wherein the asymmetric (transfer) hydrogenation reaction is performed, without intermediate isolation of the catalyst.

Suitable substrates for the asymmetric (transfer) hydrogenation are for example prochiral olefinically unsaturated compounds, in the context of this invention also referred to as olefins for short, in particular the alkylidene glycine derivatives, for example 2-acetylamino-cinnamic acid, 2-benzoylamino cinnamic acid, 2-acetylamino acrylic acid, N-acetyl-2-isopropylidene glycine, N-acetyl-2-cyclohexylidene glycine, N-acetyl-3'-methoxy-4-acetoxy-benzylidene glycine, 2-substituted maleic acids, for example 2-phenylmaleic acid, 2-methylmaleic acid; alkylidene-succinic acid derivatives, for example itaconic acid, 2-benzylidene-succinic acid, 2-isobutylidene-succinic acid;

1-substituted acrylic acid derivatives, for example 1-(6'-methoxy-naphthyl)-acrylic acid, 1-(4'-isobutylphenyl) acrylic acid, 1-substituted cinnamic acids, for example 1-methyl-cinnamic acid, 1-(hydroxymethyl)-cinnamic acid and 1-(chloromethyl)-cinnamic acid, and the salts of the above-mentioned compounds, for example the sodium, lithium, tetraalkyl ammonium or trioctyl ammonium salts and the esters, for example the methyl, the ethyl and the t-butyl esters, of dicarboxylic acids also the mono-esters can be used.

Other suitable substrates are enamides for example 1-acetamidostyrene, (Z)-2-acetyl-1-(p-methoxybenzylidene)-N-acetyl-1-(3',4'-dimethoxy-benzylidene)-6,7-dimethoxy-1,2,3,4 tetrahydro-isoquinoline, 1-benzyloxycarbonyl-4-t-butoxycarbonyl-2,3-dehydro-piperazine-2-N-t-butylamide, enol ethers, for example 1-methoxy-styrene, enol esters, for example 5-methylidene-butyrolactone, allylic alcohols, for example 3,7-dimethyl-2,7-octadiene-1-ol (geraniol), nerol, 4-hydroxy-2-cyclopentenone. A recent survey of the scope of asymmetric olefin hydrogenations is given, for example, by J. M. Brown in *Comprehensive Asymmetric Catalysis*, E. N. Jacobsen, A. Pfaltz and H. Yamamoto, eds. Springer, Berlin, 1999, Vol I, pp. 121–182.

Further suitable substrates are for example prochiral ketones having the general formula (II):

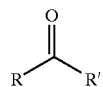

(II)

where R and R' are not equal to one another and each independently from one another represent an alkyl group, aryl group, aralkyl group, alkenyl group or alkynyl group with 1–20 C-atoms or form a ring together with the C-atom to which they are bound, it being also possible for R and R' to contain one or more heteroatoms or functional groups, for example acetophenone, 1-acetonaphthone, 2-acetonaphthone, 3-quinuclidinone, 2-methoxycyclohexanone, 1-phenyl-2-butanone, benzyl-isopropyl ketone, benzyl acetone, cyclohexyl methyl ketone, t-butylmethyl ketone, t-butylphenyl ketone, isopropyl phenyl ketone, ethyl-(2-methylethyl)-ketone, o-, m- or p-methoxyacetophenone, o-, m- or p-(fluoro, chloro,) acetophenone, o-, m- or p-cyanoacetophenone, o-, m- and/or p-trifluoromethyl-acetophenone, o-, m- or p-nitroacetophenone, 2-acetylfluorene, acetylferrocene, 2-acetylthiophene, 3-acetylthiophene, 2-acetylpyrrole, 3-acetylpyrrole, 2-acetylfuran, 3-acetylfuran, 1-indanone, 2-hydroxy-1-indanone, 1-tetralone, p-methoxyphenyl-p'-cyanophenylbenzophenone, cyclopropyl-(4-methoxyphenyl)-ketone, 2-acetylpyridine, 3-acetylpyridine, 4-acetylpyridine, acetylpyrazine, alpha-haloketones, for example alpha-chloroacetophenone; alphaketo acids, for example pyruvic acid, phenylglyoxylic acid, 4-phenyl-2-oxo-butyric acid, 3-oxo, 4,4-dimethyl-butyrolactone and esters and salts thereof; beta keto acids for example acetyl acetic acid, 4-phenylacetyl acetic acid, and esters and salts thereof; diketones, for example biacetyl, benzil, acetylacetone; hydroxyketones, for example hydroxyacetone, benzoin and 1-phenyl-1hydroxyacetone.

Other prochiral compounds that can be used in the asymmetric (transfer) hydrogenation reaction are prochiral imines having the general formula (III):

where R, R' and R" for example each independently from one another represent an alkyl group, aryl group, aralkyl group, alkenyl group, or alkynyl group with 1–20 C-atoms or form a ring together with the atoms to which they are bound, it being also possible for R, R' and R" to contain one or more heteroatoms and functional groups, and R" furthermore may be a group that can be split off, for example a phosphinyl, sulphonyl or benzyl group. Examples of imines are those prepared from the ketones described above and an alkyl amine or aryl amine or an amino acid derivative, for example an amino acid amide, an amino acid ester, a peptide or a polypeptide. Examples of a suitable alkyl amine or aryl amine are a benzyl amine, for example benzyl amine, or an o-, m- or p-substituted benzyl amine, an α-alkyl benzyl amine, a naphthyl amine, for example naphthyl amine, a 1, 2, 3, 4, 5, 6, 7 or 8- substituted naphthyl amine, a 1-(1-naphthyl)alkyl amine or a 1-(2-naphthyl)alkyl amine or a benzhydryl amine. Examples of suitable imines are N-(2-ethyl-6-methylphenyl)-1-methoxy-acetonimine, 5,6-difluoro-2-methyl-1,4-benzoxazine, 2-cyano-1-pyrroline, 2-ethyoxycarbonyl-1-pyrroline, 2-phenyl-1-pyrroline, 2-phenyl-3,4,5,6-tetrahydropyridine, 3,4-dihydro-6,7-dimethoxy-1-methyl-isoquinoline, 1-(p-methoxybenzyl)-3, 4,5,6,7,8-hexahydroisoquinoline, N-diphenylphosphinyl 2-naphtophenone imine or N-tosyl-tetralone imine.

Other prochiral compounds that can be used in the asymmetric (transfer) hydrogenation reaction are prochiral oximes and derivatives thereof having the general formula (IV):

where R and R' are as defined above, R''' for example, represents an OH-group, an ether group, an acyloxy group, a sulphonyloxy group. Examples of suitable oxime derivatives are acetophenone oxime, N-acetoxy-p-methoxyacetophenone-imine and O-methyl-p-chloroacetophenone oxime.

The catalysts according to the invention can also suitably be used in the preparation of an optically active compound, starting from a (racemic mixture of the enantiomers of an) olefin, ketone, imine or oxime derivate that contains a chiral centre elsewhere in the molecule and with preferably one of the two enantiomers being hydrogenated.

The use of the catalysts according to the invention takes place in the presence of one or more hydrogen donors, which in the context of this invention are understood to be compounds that can in some way transfer hydrogen to the substrate. Suitable hydrogen donors that can be used are preferably $H_2$, but may also be aliphatic or aromatic alcohols with 1–10 C-atoms, in particular secondary alcohols with 1–10 C-atoms, for example isopropanol or cyclohexanol, or unsaturated hydrocarbons with 5–10 C-atoms, for example 1,4 dihydrobenzene or hydroquinone, reducing sugars, for example glucose or derivates of formic acid, for example ammonium formate or an azeotropic mixture of formic acid and triethylamine.

The molar ratio of substrate to hydrogen donor preferably lies between 1:1 and 1:100. The hydrogen pressure may vary within wide limits and is preferably chosen to be as high as possible when a fast reaction or the lowest possible amount of catalyst is desired. The hydrogen pressure for example lies between 0.05 and 20 MPa, preferably between 0.1 and 10 MPa, in particular between 0.15 and 8 MPa.

In the asymmetric hydrogenation use is preferably made of a molar ratio of metal present in the transition metal compound to substrate of between 1:10 and 1:1,000,000, in particular between 1:50 and 1:100,000.

The catalyst may optionally be added in dimeric form, with the dimeric form subsequently wholly or partly changing in situ into the monomeric form.

The temperature at which the asymmetric (transfer) hydrogenation is carried out is generally a compromise between reaction velocity and enantioselectivity, and preferably lies between −20 and 120° C., in particular between 0 and 60° C. The asymmetric (transfer) hydrogenation is preferably carried out with oxygen being excluded. Preferably the substrates and solvents do not contain any oxygen, peroxides or other oxidizing substances.

As solvent use can be made of: alcohols, esters, amides, ethers, ketones, aromatic hydrocarbons, halogenated hydrocarbons. Preferably use is made of ethyl acetate, 2-propanol, acetone, tetrahydrofuran (THF), dichloromethane, toluene or dibromoethane. It is also possible to carry out the asymmetric (transfer) hydrogenation in ionic liquids as described in T. Welton, *Chem. Rev.*, 99, 2071–2083 (1999), so that isolation of the product is simplified. If necessary the solubility of the ligand in the ionic liquid can be increased by providing the ligand with polar groups such as carboxylate salts. If the substrate is a liquid, the hydrogenation can also very suitably be carried out without a solvent. If the substrate and/or the product hardly dissolves in the solvent the asymmetric (transfer) hydrogenation can also be performed as a slurry. If the product forms a slurry, its isolation is very much simplified.

Preferably the (transfer) hydrogenation reaction is carried out without preceding prehydrogenation. However, it is also possible to activate the catalyst for the asymmetric (transfer) hydrogenation prior to the addition of the substrate by hydrogenation with hydrogen or by treatment with a reducing agent, for example $NaBH_4$. The (transfer) hydrogenation reaction will sometimes also be accelerated by adding a base, an acid, a halide, or an N-hydroxyimide prior to or during the hydrogenation. Suitable bases are nitrogen bases for instance triethylamine, DBU, and substituted or non-substituted pyridines and mineral bases for example KOtBu or $Cs_2CO_3$. Suitable acids are for example HBr, trifluoroacetic acid. Suitable halides are for example alkali halides or tetraalkylamonium halides e.g. LiI, LiBr, LiCl, NaI, tetrabutylammonium iodide. A suitable N-hydroxy-imide is for instance N-hydroxy-phtalic-imide.

The invention will be elucidated with reference to the following examples, without however being restricted by these:

EXAMPLES

Example I

Synthesis of Ligand 1

Under a slow nitrogen gas flow 7 mL (38 mmol) of hexamethylphosphorus triamide was added to a suspension of 10.0 g of S—(−)-1,1'bi-2-naphthol (34.9 mmol) in 50 g of dry toluene at 40° C. After 1 minute the product started to crystallize. After 5 hours the solid was removed by filtration, washed with toluene and pentane and dried. Yield: 11.0 g (30.6 mmol, 88%), pure product according to TLC (silica gel, EtOAc:hexane=1:1, $^{31}$P-NMR and $^1$H-NMR).

Example II

Synthesis of Ligand 2

A suspension of 0.36 g of ligand 1 (1.0 mmol), 0.07 g of tetrazole (0.9 mmol) and 0.394 mL of dibenzyl amine (2.0 mmol) in 4 mL of dry toluene was boiled for 5 hours with reflux under a slow nitrogen gas flow. Afterwards the solution was cooled and filtered over a thin layer of silica gel. After washing of the silica gel with 10% t-BuOMe in hexane the filtrate was thoroughly evaporated. Yield: 0.44 g (0.87 mmol, 87%), pure according to $^{31}$P-NMR and $^1$H-NMR and TLC.

Example III

Synthesis of Ligand 3

To a cooled solution (−60° C.) of $PCl_3$ (3.0 mmol), $Et_3N$ (6.0 mmol) and toluene (5 mL) was added a warm solution (60° C.) of (S)-2,2-binaphthol (3.0 mmol) and toluene (25 mL) in 5 min. After stirring for 2 h the reaction mixture was warmed to room temperature and filtered under an argon atmosphere. The filtrate was treated with $Et_3N$ (2.9 mmol) and 2.9 mmol of (R,R)-bis-(1-methylbenzyl)-amine at −40° C. After 16 h at ambient temperature, the reaction mixture was filtered, concentrated and purified by chromatography. Yield: 41%, pure according to $^{31}$P-NMR and $^1$H-NMR and TLC.

Example IV

Hydrogenation of Olefins

Method A. Hydrogenation at 0.1 MPa with Prehydrogenation $Rh(COD)_2BF_4$ (0.010 mmol) and chiral ligand (0.022 mmol) were weighed into a 10 ml Schlenk vessel, a magnetic stirring bar was added and the vessel was closed with a rubber septum. 3 Vacuum/nitrogen cycles were followed by 2 vacuum/hydrogen cycles. 1.5 mL of solvent is added and stirring under a hydrogen atmosphere of 0.1 MPa takes place for 1 hour. Subsequently a solution of substrate (0.2 mmol) in 3.5 ml solvent is added and the reaction mixture is stirred under a hydrogen atmosphere. Samples were filtered over silica gel with EtOAc: hexane 4:1 and evaporated. The e.e. was determined by chiral GC or HPLC, the conversion by $^1$H-NMR. When the reaction was finished the reaction mixture was treated and evaporated, in the same way as the samples. Results are depicted in the Tables.

Method B. Hydrogenation Experiment at 0.1 MPa (without Prehydrogenation)

Rh(COD)$_2$BF$_4$ (0.010 mmol), chiral ligand (0.022 mmol) and substrate (0.2 mmol) were weighed into a Schlenk tube equipped with a rubber septum cap and a stirring bar. After three vacuum/nitrogen cycles 5 mL of freshly distilled solvent is added through the septum cap and the reaction mixture is stirred under a hydrogen atmosphere of 0.1 MPa. Samples and reaction mixture were treated as described in method A. Results are depicted in the Tables.

Method C. Hydrogenation at 0.5 MPa

Rh(COD)$_2$BF$_4$, chiral ligand (2.2. molequivalents in respect to Rh), and CH$_2$Cl$_2$ (10 mL) were added into a Schlenk vessel and stirred under a nitrogen atmosphere. The catalyst solution was transferred to a 50 mL Buchi miniclave by using a syringe. When solvents other than CH$_2$Cl$_2$ were applied in the hydrogenation, Rh(COD)$_2$BF$_4$ and chiral ligand were first dissolved in CH$_2$Cl$_2$ by stirring at RT under a nitrogen atmosphere for 10 minutes, CH$_2$Cl$_2$ was evaporated under vacuum, the desired solvent (10 mL) was added and subsequently this catalyst solution was transferred to the Buchi miniclave.

In a number of cases this solution was prehydrogenated for 1 hour under a hydrogen atmosphere of 0.1 MPa. The substrate (0.8 mmol) dissolved in 10 mL solvent was added to the Buchi miniclave and a hydrogen pressure of 0.5 MPa was applied. Samples and reaction mixture were treated as described in method A. Results are depicted in the Tables.

Method D. Hydrogenation at 6 MPa

Rh(nbd)$_2$BF$_4$ (4.0 mg, 0.0099 mmol) and 8.6 mg of chiral ligand 1 (0.022 mmol) were dissolved under a nitrogen atmosphere in CH$_2$Cl$_2$ (2.5 mL, degassed) in a Schlenk tube equipped with a magnetic stirrer and septum cap. The orange solution was stirred for 5 minutes at room temperature, and the solvent was removed by evaporation. The catalyst was dissolved in of EtOAc (20 mL, degassed). α-Acetamidocinnamic acid ester (240 mg, 1.09 mmol) was added to a 125 ml Parr autoclave. After three nitrogen pressure (0.29 MPa)—pressure release cycles EtOAc (30 ml) was added. The orange catalyst solution (20 ml) was added to the autoclave by using a syringe and a hydrogen pressure of 6.0 MPa was applied. The reaction mixture was stirred at 680 rpm using an overhead stirrer with a propeller stirring blade. Samples were taken after 4, 10 and 20 minutes. The reaction proved to be completed after 4 minutes. The conversion to N-acetyl-phenylalanine methyl ester was >99% with an e.e. of 97%. See also Table 2.

Method E. Hydrogenation of Different Olefins and Enamides at Different Hydrogen Pressures Rh(COD)$_2$BF$_4$, chiral ligand (2.2 molequivalent to Rh), substrate, and solvent were weighed into an autoclave. The autoclave was closed and inertised by three nitrogen pressure (0.29 MPa)—pressure release cycles. The desired hydrogen pressure was applied and the reaction mixture was stirred at 500 rpm using an overhead stirrer with a propeller stirring blade. The reactions were monitored by hydrogen uptake. Results are depicted in Table 6.

TABLE 1

| L* | Lig. Conf. | Method | Temp. °C. | Solvent | Time (min) | Conv. (%) | E.e. (%) | Prod. Conf. |
|---|---|---|---|---|---|---|---|---|
| 1 | S | A | RT | MeOH | 1080 | 60 | 72 | R |
| 1 | R | A | RT | MeOH | 1320 | 98 | 75 | S |
| 1 | R | A | RT | CH$_2$Cl$_2$ | 240 | 100 | 94.7 | S |
| 1 | S | A | RT | CH$_2$Cl$_2$ | 240 | 100 | 95.5 | R |
| 1 | S | A | RT | EtOAc | 120 | >98 | 91.2 | R |
| 1 | S | A | 5 | CH$_2$Cl$_2$ | 180 | 96 | 97.2 | R |
| 1 | S | A | -10 | CH$_2$Cl$_2$ | 1080 | 86 | 98.0 | R |
| 1 | S | A | -10 | CH$_2$Cl$_2$ | 1080 | 92 | 97.9 | R |
| 1 | S | A | RT | ClCH$_2$CH$_2$Cl | 120 | >98 | 88.9 | R |
| 1 | S | A | RT | Acetone | 270 | 92 | 92.4 | R |
| 1 | S | A | RT | THF | 270 | 75 | 93.6 | R |
| 1 | S | B | RT | ClCH$_2$CH$_2$Cl | 300 | 100 | 96.0 | R |
| 1 | S | B | RT | CH$_2$Cl$_2$ | 120 | 94 | 97.0 | R |
| 1 | S | B | RT | EtOAc | 300 | >98 | 95.6 | R |
| 1 | S | A | RT | CH$_2$Cl$_2$ + 50 mL H$_2$O | 240 | 100 | 92.2 | R |
| 1 | S | B | 0 | CH$_2$Cl$_2$ | 1200 | 100 | 97.6 | R |
| 1 | S | B | 0 | EtOAc | 1200 | 85 | 98.4 | R |
| 1 | S | B | 0 | ClCH$_2$CH$_2$Cl | 1200 | 100 | 97.6 | R |
| 1 | S | B | -10 | CH$_2$Cl$_2$ | 1200 | 64 | 97.9 | R |
| 2 | S | A | RT | MeOH | 1260 | 16 | 56 | R |
| 3 | S,R,R | A | RT | CH$_2$Cl$_2$ | 240 | 100 | 42 | R |
| 6 | S | A | RT | MeOH | 11520 | 72 | 34 | R |
| 13 | R,R | A | RT | MeOH | 240 | 100 | 37 | R |
| 14 | R,R | A | RT | MeOH | 1440 | 100 | 77 | S |

TABLE 2

Hydrogenation of 2-acetamido-cinnamic acid methyl ester with chiral ligand 1 at elevated pressure (see Example IV)

| Method | Prehydro-genation | Temp. (° C.) | Solvent | Amount of Rh (mol %) | Time (min) | Conversion (%) | E.e (%) |
|---|---|---|---|---|---|---|---|
| C | Yes | RT | $CH_2Cl_2$ | 5 | 10 | >98 | 94.6 |
| C | Yes | −5 | $CH_2Cl_2$ | 5 | 60 | >98 | 97.2 |
| C | Yes | RT | $CH_2Cl_2$ | 0.5 | 40 | >98 | 94.7 |
| C | No | RT | $CH_2Cl_2$ | 0.5 | 60 | 87 | 95.5 |
| C | No | RT | Acetone | 0.5 | 60 | 94 | 95.5 |
| C | Yes | RT | EtOAc | 0.5 | 60 | 58 | 95.7 |
| C | No | RT | THF | 5 | 30 | >98 | 95.9 |
| D | No | RT | EtOAc | 0.9 | 4 | >98 | 97 |

TABLE 4

Hydrogenations of various olefins using the catalyst of the invention (see Example IV, method B, Conv. >99%).

$R^3-CH=C(CO_2R^4)(NHAc) \xrightarrow{Rh(COD)_2BF_4, \text{chiral ligand 1}} R^3-CH_2-C^*H(CO_2R^4)(NHAc)$

| $R^3$ | $R^4$ | Temp (° C.) | Solvent | Time (min) | E.e (%) |
|---|---|---|---|---|---|
| H | Me | 0 | EtOAc | 1200 | >99 |
| Ph | H | RT | EtOAc | 1200 | 80 |
| H | Me | RT | $CH_2Cl_2$ | 240 | >99 |
| H | Me | RT | EtOAc | 960 | >99 |
| H | H | RT | EtOAc | 180 | 99 |
| (p-OAc, m-OMe)-Ph | Me | RT | EtOAc | 1200 | 94 |
| (p-OAc, m-OMe)-Ph | Me | RT | $CH_2Cl_2$ | 1200 | 95 |
| (p-OAc, m-OMe)-Ph | Me | 0 | EtOAc | 1200 | 98 |
| (p-OAc, m-OMe)-Ph | Me | 0 | $CH_2Cl_2$ | 1200 | 96 |
| (p-F)-Ph | H | RT | EtOAc | 270 | 76 |
| (p-F)-Ph | Me | RT | $CH_2Cl_2$ | 150 | 95 |

TABLE 5

Hydrogenations of itaconic acid and derivatives using the catalyst of the invention (see Example IV, at RT).

| $R^5$ | $R^6$ | Method | Solvent | Time (min.) | Conv. (%) | E.e. (%) |
|---|---|---|---|---|---|---|
| Me | Me | A | $CH_2Cl_2$ | 780 | >99 | 87 |
| H | H | B | EtOAc | 1200 | >99 | 97 |
| Me | Me | B | $CH_2Cl_2$ | 1200 | >99 | 94 |
| H | H | B | $CH_2Cl_2$ | 1200 | >99 | 95 |
| Me | Me | C, No prehydrog., 0.5 mol % Rh | $CH_2Cl_2$ | 60 | 75 | 91 |

TABLE 6

Hydrogenations of enamides using the catalyst of the invention (see Example IV, in $CH_2Cl_2$, at RT, conv. >99%).

| $R^7$ | Ligand | Method | Amount of Rh (mol %) | Hydrogen Pressure (MPa) | Time (min.) | E.e. (%) |
|---|---|---|---|---|---|---|
| H | 1 | B | 5 | 0.5 | 1200 | 92 |
| p-Cl | 2 | E | 2 | 1.5 | 210 | 58 |
| p-Cl | 20, $R^1$ and $R^2$ = Me | E | 2 | 1.5 | 210 | 89 |
| p-Cl | 22, $R^1$ and $R^2$ = Me | E | 2 | 1.5 | 210 | 86 |
| p-Cl | 1 | E | 2 | 1.5 | 210 | 93 |
| p-Ome | 1 | E | 2 | 1.5 | 240 | 84 |
| p-Ome | 22, $R^1$ and $R^2$ = Me | E | 2 | 1.5 | 240 | 62 |
| p-Ome | 20, $R^1$ and $R^2$ = Me | E | 2 | 1.5 | 240 | 83 |
| p-Ome | 2 | E | 2 | 1.5 | 240 | 53 |

Comparative Experiment

Hydrogenation with chiral bidentate ligands (not forming part of the invention). Hydrogenation of 2-acetamidocinnamic acid methyl ester according to method A (See Example IV), with 1.1 molequivalent of chiral ligand, unless stated otherwise). The results are given in Table 3. The results show that bidentate phosphoramide ligands generally lead to slow reactions with low enantioselectivity.

TABLE 3

| L* | Lig. Conf. | Remarks | Solvent | Time (min.) | Conv. (%) | E.e. (%) | Prod. Conf. |
|---|---|---|---|---|---|---|---|
| 28 | S,S | | MeOH | 1140 | 100 | 22 | R |
| 28 | S,S | | $CH_2Cl_2$ | 1140 | 100 | 42 | R |
| 29 | R,R | | MeOH | 1380 | 6 | 52 | R |
| 29 | R,R | 2.2 eq. ligand | MeOH | 1320 | — | — | — |
| 29 | R,R | | $CH_2Cl_2$ | 1440 | 56 | 72 | R |
| 30 | S,S | | MeOH | 1380 | — | — | — |
| 30 | S,S | 2.2 eq. ligand | MeOH | 1320 | — | — | — |
| 30 | S,S | | $CH_2Cl_2$ | 1440 | 100 | 25 | S |
| 31 | R,S,R,S | | MeOH | 1260 | 18 | 12 | S |
| 31 | R,S,R,S | | $CH_2Cl_2$ | 1440 | 7 | 28 | R |
| 32 | S,S,S,S | | MeOH | 1260 | 40 | 6 | R |
| 32 | S,S,S,S | | $CH_2Cl_2$ | 1440 | 100 | 80 | S |
| 33 | R,R,R,R | | MeOH | 1320 | 100 | 14 | S |
| 34 | R,R,R,R | | MeOH | 1320 | 40 | 15 | S |

Bidentate ligands, not forming part of the invention

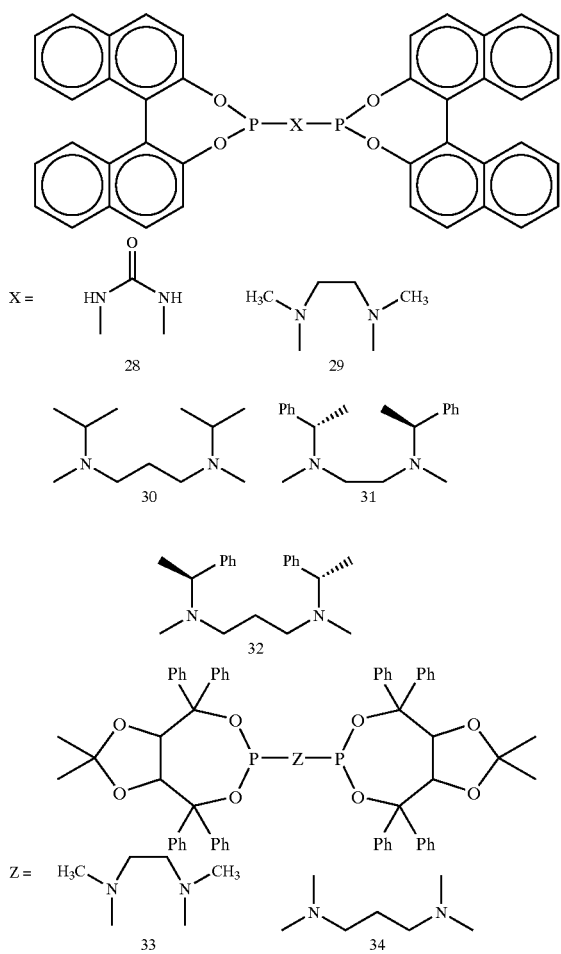

Example V

Hydrogenation of Acetophenone
Synthesis of the Catalyst Complex Ru(ligand)(diamine)Cl$_2$
[RuCl$_2$(p-cymene)]$_2$ (9 mg) and 2 equiv. of the ligand 1 (21.9 mg) were put in a schlenk-flask under N$_2$-atmosphere. DMF (1.0 ml) was added and the mixture was degassed by 3 vacuum/N$_2$ cycles. Then it was stirred at 65° C. for 16–24 h (or 3 h 90° C.). A RuCl$_2$(ligand)$_2$(dmf)$_n$ complex is formed. Then it is cooled to r.t. and 1 equiv. of (S,S)-1,2-diphenyl-1,2-diaminoethane (DPEN) (6.3 mg) was added. After stirring the mixture for another 16–24 h it was used for hydrogenation.
Spectroscopic data: RuCl$_2$(ligand)$_2$(dmf)$_n$ P-NMR: 148.8 ppm;
Ru(ligand)(DPEN)Cl$_2$ P-NMR: 147.7 (free ligand) and 172.2 (complex) ppm.
Preformed complex of formula Ru(L)Cl$_2$[(S,S)-1,2-diphenylethylenediamine] (0.1 mmol), and substrate (10 mmol), were weighed into an autoclave. Under a slow nitrogen flow degassed MeOH (50 mL) and K$_2$CO$_3$ (2.0 mmol) were added and the autoclave was closed and inertised by three nitrogen pressure (0.29 MPa)—pressure release cycles. The desired hydrogen pressure (5.0 MPa) and temperature (50° C.) were applied and the reaction mixture was stirred at 500 rpm using an overhead stirrer with a propeller stirring blade.

Results:
L=Ligand 1: after 45 min, 93% conversion, with 58% e.e.
L=Ligand 1 wherein the N-methyl groups are replaced by i-propyl groups: after 150 min, 98% conversion, with 67% e.e.

Example VI

Asymmetric Transfer Hydrogenation Using Ruthenium(II) and Iridium(I) Complexes of Ligand 1

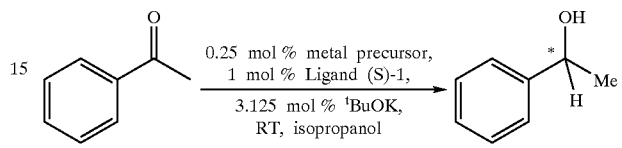

Asymmetric Reduction of Acetophenone Using an Iridium (I) Catalyst
A mixture of [IrCl(cod)]$_2$ (0.01 mmol, 0.25 mol %, 6.7 mg) and (S)-1 as a ligand (0.04 mmol, 1 mol %, 14.4 mg) in dry, degassed isopropanol (5 ml) was heated at 80° C. for 1 h under nitrogen. After cooling to room temperature, the catalyst solution was added to a solution of potassium tert-butoxide (0.125 mmol, 3.125 mol %, 14.0 mg) and acetophenone (4 mmol, 471 μl) in dry, degassed isopropanol (35 ml). The reaction was stirred at room temperature under nitrogen for the time indicated and monitored by GC analysis. Results are given in Table 7.
Asymmetric Reduction of Acetophenone Using a Ruthenium(II) Catalyst
A mixture of [RuCl$_2$(p-cymene)]$_2$ (0.0125 mmol, 0.25 mol %, 7.7 mg) and (S)-Monophos as a ligand (0.05 mmol, 1 mol %, 18.0 mg) in dry, degassed isopropanol (5 ml) was heated at 80° C. for 1 h under nitrogen. After cooling to room temperature, the catalyst solution was added to a solution of potassium tert-butoxide (0.15 mmol, 3 mol %, 16.8 mg) and acetophenone (5 mmol, 588 μl) in dry, degassed isopropanol (40 ml). The reaction was stirred at room temperature under nitrogen for the time indicated and monitored by GC analysis.
Results are given in Table 7.

TABLE 7

Asymmetric transfer hydrogenation of acetophenone with isopropanol catalysed by ruthenium and iridium complexes.

| Metal precursor | Time (h) | Conversion (%) | ee (major enantiomer) |
| --- | --- | --- | --- |
| [IrCl(cod)]$_2$ | 1.5 | 8 | 25 (R) |
|  | 21 | 51 | 27 (R) |
| [RuCl$_2$(p-cymene)]$_2$ | 1 | 17 | 47 (R) |
|  | 21 | 24 | 46 (R) |

What is claimed is:
1. A compound of the formula

ML$_a$X$_b$S$_c$, wherein M is rhodium or ruthenium;
X is a counter ion;
S is a ligand;
a is 0.5–3; b and c each independently is 0 to 2; and
wherein L is a chiral ligand having one phosphorus atom of the formula

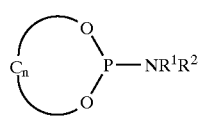

(I)

wherein $C_n$ is substituted or unsubstituted alkylene of 2–4 C-atoms;

$R^1$ and $R^2$ are each independently H, an optionally substituted alkyl, aryl, alkaryl or aralkyl or $R^1$ and $R^2$ form a heterocyclic ring together with the N-atom to which they are bound.

2. The compound of claim 1, wherein $C_n$ represents a chiral substituted $C_4$ chain that has substantially one particular configuration.

3. The compound of claim 2, wherein $C_n$ represents two pairs of adjacent C-atoms wherein each pair forms part of an aryl group or of a naphthyl group.

4. The compound of claim 1 wherein $R^1$ and $R^2$ are independently alkyl.

5. The compound of claim 1, comprising a chiral ligand selected from the group consisting of 1
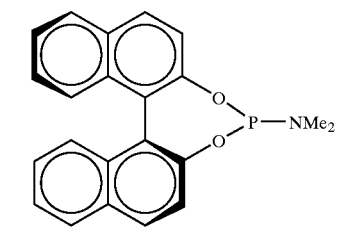

2
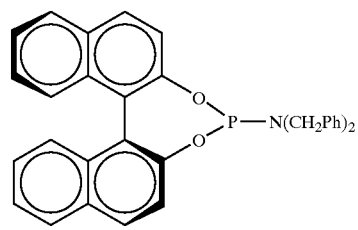

3
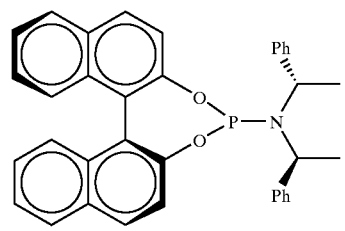

4
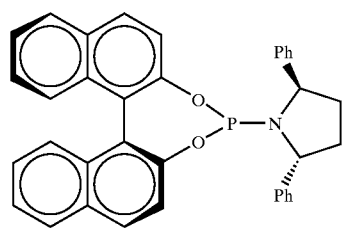

5
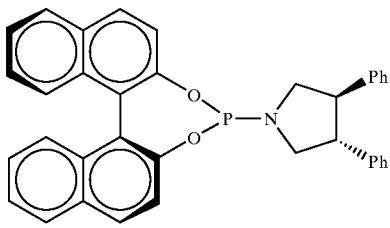

6
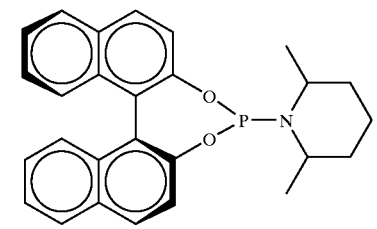

2a
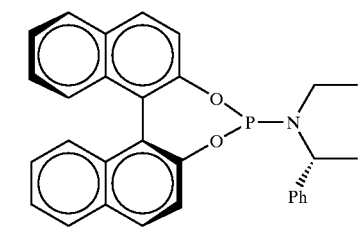

7
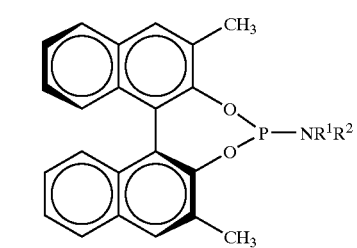

8
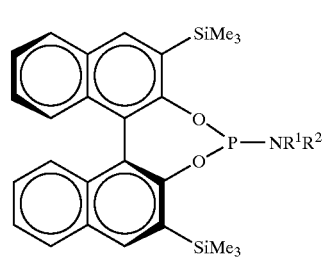

9
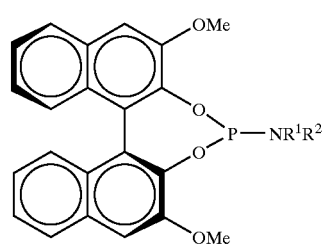

10
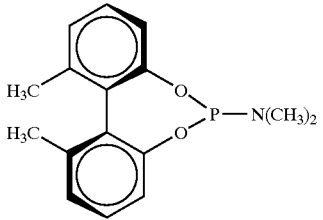

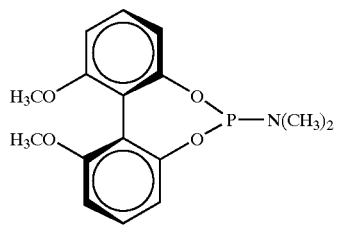
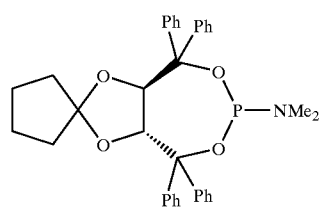
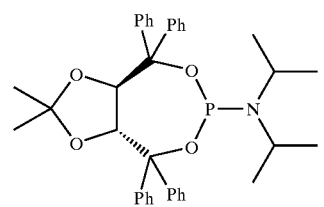
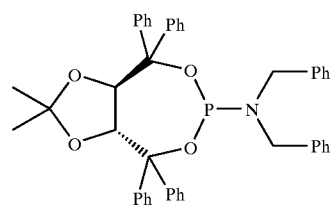
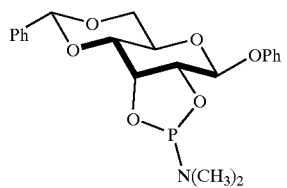
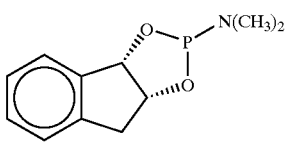
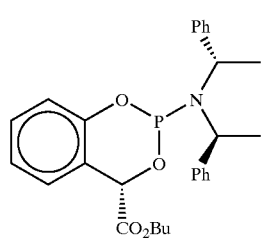
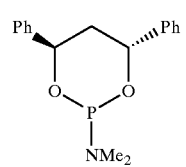
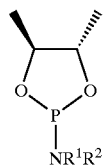
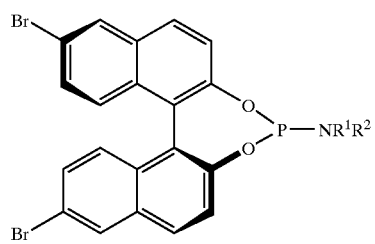
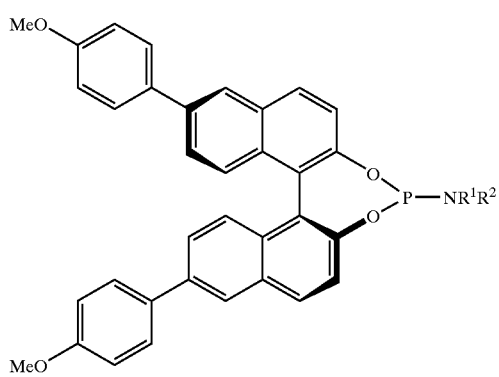
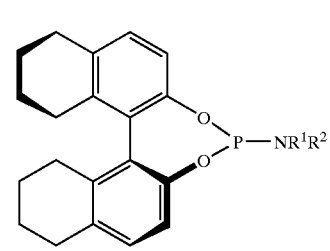
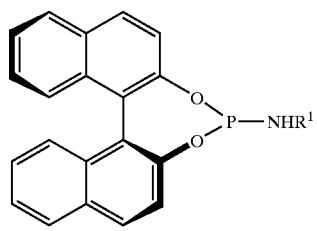
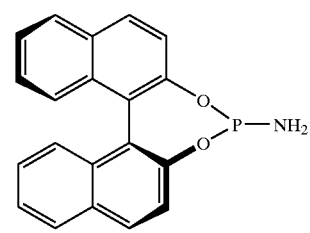

-continued

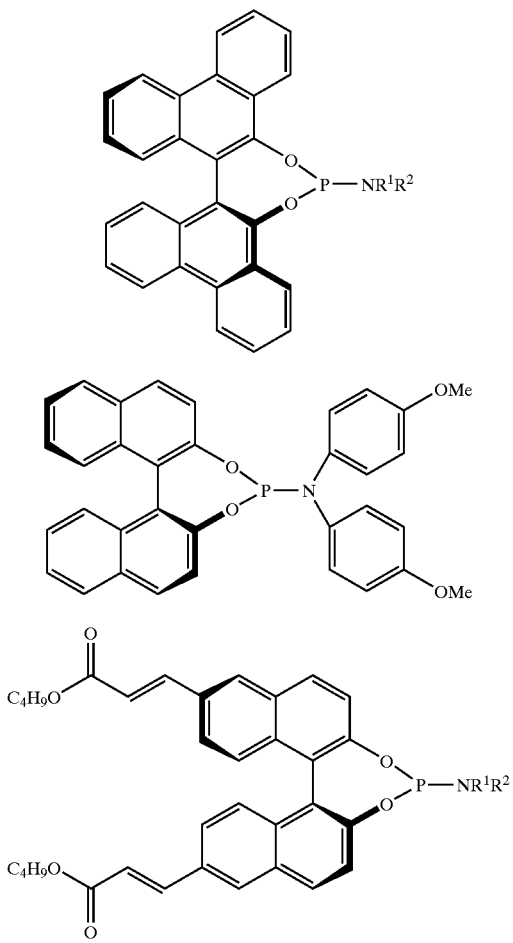

wherein each R¹ and R² is as defined in claim 1.

6. A method for the preparation of a ligand of formula (1) as defined in claim 1, which method comprises
   (a) reacting a diol having the formula HO—$C_n$—OH where $C_n$ is as defined in claim 1 with $P(N(R^3)_2)_3$ wherein R³ is methyl or ethyl, followed by;
   (b) treating the resultant of (a) with R¹R²NH, wherein R¹ and R² are each independently optionally substituted alkyl, aryl, alkaryl or aralkyl or together form a heterocyclic ring with the N-atom to which they are bound.

7. A process for the asymmetric hydrogenation or asymmetric transfer hydrogenation, comprises treating a substrate with a hydrogen donor in the presence of a compound having formula $$ML_aX_bS_c,$$

wherein M is rhodium or ruthenium;
L, X, S, a, b and c are as defined in claim 1, to form a product.

8. The process of claim 7 wherein said substrate is an olefinically unsaturated compound, a ketone, an oxime, or an imine.

9. The process of claim 7 wherein $C_n$ in formula 1 represents a chiral substituted $C_4$ chain that has substantially one particular configuration.

10. The process of claim 9 wherein $C_n$ represents two pairs of adjacent C-atoms wherein each pair forms part of an aryl group or of a naphthyl group.

11. The process of claim 7 which is carried out in the presence of a non-protic solvent.

12. The process of claim 7 which is carried out in the presence of an ionic liquid.

13. The process of claim 7 wherein the hydrogen donor is selected from the group consisting of hydrogen, isopropanol and a mixture of formic acid and triethylamine.

14. The process of claim 7 which is carried out at a pressure of between 0.1 and 10 MPa.

15. The process of claim 7 wherein the substrate is an olefin, a ketone or an imine and wherein said substrate contains a chiral centre.

16. The process of claim 7 wherein compound having formula $ML_aX_bS_c$ is prepared in situ.

17. The process of claim 7, further comprising treating said substrate in a solvent, wherein the substrate and/or the product forms a slurry with the solvent.

18. The compound of claim 1, comprising the chiral ligand

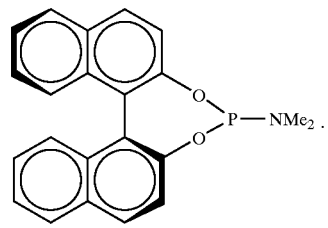

* * * * *

UNITED STATES PATENT AND TRADEMARK OFFICE
CERTIFICATE OF CORRECTION

PATENT NO. : 6,989,461 B2
DATED : January 24, 2006
INVENTOR(S) : Michel Berg Van Den et al.

It is certified that error appears in the above-identified patent and that said Letters Patent is hereby corrected as shown below:

<u>Column 23,</u>
Line 51, change "comprises" to -- comprising --.

Signed and Sealed this

Eleventh Day of April, 2006

JON W. DUDAS
*Director of the United States Patent and Trademark Office*

UNITED STATES PATENT AND TRADEMARK OFFICE
CERTIFICATE OF CORRECTION

PATENT NO. : 6,989,461 B2
APPLICATION NO. : 10/332403
DATED : January 24, 2006
INVENTOR(S) : Van Den Berg et al.

It is certified that error appears in the above-identified patent and that said Letters Patent is hereby corrected as shown below:

Column 24, line 7, delete "rhodium or ruthenium;" and replace by inserting --rhodium, iridium or ruthenium; and--.

Signed and Sealed this

First Day of June, 2010

David J. Kappos
*Director of the United States Patent and Trademark Office*